(12) United States Patent
Calkins (10) Patent No.: US 9,132,283 B2
(45) Date of Patent: Sep. 15, 2015

(54) PERFORATED NONSLIP NON-ADHESIVE SURFACE COVERING

(75) Inventor: Mark A Calkins, San Jacinto, CA (US)

(73) Assignee: KITTRICH CORPORATION, La Mirada, CA (US)

(*) Notice: Subject to any disclaimer, the term of this patent is extended or adjusted under 35 U.S.C. 154(b) by 161 days.

(21) Appl. No.: 13/022,468

(22) Filed: Feb. 7, 2011

(65) Prior Publication Data

US 2012/0183726 A1 Jul. 19, 2012

Related U.S. Application Data (60) Provisional application No. 61/432,903, filed on Jan. 14, 2011.

(51) Int. Cl.

| B32B 3/24 | (2006.01) |
|---|---|
| A61N 5/10 | (2006.01) |
| A61B 6/03 | (2006.01) |
| A61B 6/04 | (2006.01) |
| A61B 6/00 | (2006.01) |

(52) U.S. Cl.
CPC .............. *A61N 5/1039* (2013.01); *A61B 6/032* (2013.01); *A61B 6/0457* (2013.01); *A61B 6/405* (2013.01); *A61B 6/4085* (2013.01); *A61B 6/481* (2013.01); *A61B 6/482* (2013.01); *A61B 6/507* (2013.01); *A61B 6/541* (2013.01); *A61N 5/103* (2013.01); *Y10T 156/1041* (2015.01); *Y10T 156/1057* (2015.01); *Y10T 428/24322* (2015.01); *Y10T 428/24496* (2015.01); *Y10T 428/249953* (2015.04); *Y10T 428/249982* (2015.04); *Y10T 428/249987* (2015.04); *Y10T 428/249992* (2015.04); *Y10T 428/249993* (2015.04)

(58) Field of Classification Search
CPC .............................. B23B 2/266; Y10T 428/15
USPC .................................................... 428/43, 172
See application file for complete search history.

(56) References Cited

U.S. PATENT DOCUMENTS

| 3,143,208 | A |   | 8/1964 | Sizemore |   |
|---|---|---|---|---|---|
| 4,465,729 | A | * | 8/1984 | Cancio et al. | 428/167 |
| 5,198,275 | A |   | 3/1993 | Klein |   |
| 5,854,144 | A |   | 12/1998 | Hawley |   |
| 6,007,886 | A |   | 12/1999 | Takigami |   |
| 6,238,762 | B1 |   | 5/2001 | Friedland et al. |   |
| 6,505,444 | B1 |   | 1/2003 | Johnson |   |
| 2003/0152761 | A1 |   | 8/2003 | McCune |   |
| 2005/0037190 | A1 |   | 2/2005 | Browne et al. |   |
| 2006/0127628 | A1 | * | 6/2006 | Price | 428/41.8 |
| 2009/0004433 | A1 | * | 1/2009 | Privitera et al. | 428/143 |

OTHER PUBLICATIONS

International Search Report for PCT/US12/21213 dated May 4, 2012.

* cited by examiner

*Primary Examiner* — Alexander Thomas
(74) *Attorney, Agent, or Firm* — Leason Ellis LLP (57) ABSTRACT

A surface covering that is a multilayered composite material. The multilayer composite material includes a top facing layer of polymeric film and a bottom layer of unsupported foam.

14 Claims, 6 Drawing Sheets

PERFORATED NONSLIP NON-ADHESIVE SURFACE COVERING

RELATED APPLICATION DATA

The present application claims priority to provisional application 61/432,906 filed in the United States Patent Office on Jan. 14, 2011, the entirety of which is hereby incorporated by reference herein to the extent permitted by law.

BACKGROUND OF THE INVENTION

1. Field of the Invention

The present invention is directed to removable, nonslip, non-adhesive coverings which are used as shelf, drawer or storage liners. In particular, the covering sheet features an improved composite material having a top decorative layer of polymeric film combined to a continuous bottom layer of unsupported foam. The structure of the multilayered composite material facilitates the convenient hand tearing of the sheet to size through a grid of perforations oriented along the vertical and horizontal axes of the covering.

2. Description of the Prior Art

Shelf, drawer or storage liners have been extensively sold at retail venues and are available in a selection of self-adhesive or non-adhesive coverings. Printed wall coverings or papers were once used to protect the wooden interiors of cabinets or drawers from exposure to moisture. These permeable materials were eventually replaced with the application of decorative self-adhesive plastic sheets, which provide a greater degree of water resistance to the unfinished or varnished surfaces of cupboards. Self-adhesive shelf liners primarily consist of a facing layer of transparent, opaque or printed polymeric film coated with an underlying layer of pressure sensitive adhesive. The pressure sensitive adhesive may be combined with a siliconized release liner, which is removed prior to the application of the decorative plastic laminate. To assist the consumer in the installation of the product, the release liner typically features an imprinted grid of guide lines following the vertical and horizontal axes of the covering. The interior dimensions of cabinets or drawers are then transferred to the printed release liner prior to cutting the shelf liner to size.

Another provision known in the art includes a decorative laminate having a releasable first face with an adhesive coated reverse face, thereby permitting the sheet to be rolled upon itself and readily unrolled without the need for a separable siliconized liner. In one variation, the covering may consist of a polypropylene film having a fine pattern of micro-embossed indentations formed into the exterior facing of the sheet. The micro-embossed pattern reduces the surface area of the laminate and limits the corresponding degree of contact with the adhesive layer when wound into rolls for retail distribution. Alternatively, transparent varnishes containing an admixture of polymerized siloxanes, which are more commonly referred to as polysiloxanes, have been applied to create a releasable decorative layer for self-adhesive shelf liners made from paper or polymeric materials. Although the use of silicone coatings or micro-embossed indentations enhance the smooth separation of pressure sensitive laminates, the installation of such self-wound materials can be very troublesome in poorly accessed locations. The omission of a printed release liner eliminates the efficient means for preparing the self-adhesive covering to fit within the confined interiors of cabinets or drawers. Instead, it is necessary to first adhere the self-wound sheeting to an uncovered surface, while folding any remaining edge portions up along the adjacent walls of a cupboard, then subsequently trimming away the excess material with a razor blade.

In the prior art, the application of self-adhesive coverings are known to become frequently unmanageable. It is difficult to accurately achieve consistent straight cuts along the length and width of the material, even with the added convenience of an imprinted release liner, and especially when the shelf liner is self-wound. Irregular, oversized or non-conforming laminates that will not precisely adhere to their intended surfaces may result in the formation of entrapped air pockets beneath these impermeable coverings. Such air pockets eventually collapse under load, permanently causing unsightly creases and wrinkles Moreover, a further problem emerges when the exposed adherent layer inadvertently folds upon itself, as the separation of these mutually bonded surfaces results in the irreparable deformation of the polymeric film.

Previous attempts have been made in the prior art to simplify the alteration of self-adhesive shelf liners so that they may correspond to the dimensions of cabinets and drawers. For example, earlier methods include the provision of forming lines of weakness into a laminate sheet to facilitate the hand-tearing of the covering to fit a surface of predetermined size.

U.S. Pat. No. 6,238,762, issued on May 29, 2001 to R. Friedland et al., discloses a self-adhesive decorative covering adapted with through-cut microperforations and embossed prescores, which are oriented at right angles, to provide rectilinear yield lines enabling the manual hand sizing of a sheet. Lines of weakness may also run diagonally between the grid of microperforations to facilitate changes in the direction of tearing. The disclosure further includes a provision for extending the embossed prescores partially through the profile of the laminate. The arrangement of through-cut microperforations and embossed prescores may be used in combination with a self-adhesive covering having a separable release liner that includes a corresponding pattern of perforations or, alternatively, with a self wound sheet having a releasable polysiloxane facing.

U.S. Pat. Nos. 4,380,564 and 4,465,729, issued on Apr. 19, 1983 and Aug. 14, 1984, respectively, to Cancio et al., disclose a plastic laminate having an intersecting grid of tear lines formed into the surface of the sheet material whereby the film may be torn by hand in more than one direction. In a preferred embodiment presented in both patents, the plastic sheet materials are composed of a polymeric component consisting of a low density polyethylene having a disperse phase of calcium carbonate, with the preferred ratio of the foregoing ingredients contingent upon the dimension of the grid pattern embossed into the film. The inventors claim that the selected admixtures of polyethylene and calcium carbonate enhance the tear assisting provision of their polymeric sheet while maintaining the overall tensile strength characteristics of the material. In each disclosure, a layer of adhesive may be disposed on one side of the plastic covering, which is protected by a release liner that does not have any cross-tearable lines. Accordingly, installation of the materials taught in both patents first requires the removal of the release liner prior to hand tearing the laminate to size.

The primary disadvantage of the prior art, inherent within self-adhesive coverings which integrate perforated or cross-tearable features, concerns the inadvertent separation of the shelf liner along unselected lines of weakness, especially when attempting to pull apart mutually adhering surface portions that have accidentally folded upon themselves. The strong reciprocal bond created through such mishaps may surpass the tensile strength property of the yield lines, causing the unintended fragmentation of the plastic sheet, thereby rendering the covering unsuitable for installation. Moreover, another difficulty relates to the replacement of perforated or cross-tearable laminates after long-term use, as the molecular structure of the polymeric film degrades with age, while the self-adhesive coating becomes fully cured to the interior surfaces of cabinets or drawers. Consequently, the increased bond strength of the adhesive, combined with the embrittlement of the plastic, will result in the adverse disintegration of the material into miniscule pieces upon removal.

Although the use of self-adhesive coverings in the prior art have long provided consumers with the means to both decorate and protect shelving and drawers, the thin layer of polymeric film often fails to conceal uneven surface flaws or irregularities. More recently, the renovation or construction of kitchens and bathrooms now feature cabinets with water-resistant interior laminates, sold commercially under the Wilsonart® or Formica® brands, which are primarily manufactured from thermosetting plastic resins. Since the latest cabinet fabrications also use composite particle board materials, the application of such laminates inhibits moisture from coming into contact with the bonded wooden fibers and produces a smooth consistent surface that can be easily cleaned. Where functionality and durability is therefore enhanced, the thermoset resin permanently hardens under heat and pressure during the formation of these laminates, thereby increasing the rigidity while diminishing the impact resistance of the material. Without the benefit of a suitable protective covering, the striking force of ordinary household articles can cause pieces of the thermoset plastic sheet to break away from shelving or drawers. In view of the fact that self-adhesive coverings offer superficial protection against impact resistance, and their subsequent removal often leaves behind a viscous residue, non-adhesive shelf liners have gained widespread acceptance.

One type of non-adhesive shelf liner in the prior art consists of a knitted polyester scrim with a coating of thermally foamed polyvinyl chloride (PVC) resin. The knitted construction of the scrim provides an arrangement of woven yarns defining a pattern of apertures that correspond to a configuration of openings extending through the thickness of the cured PVC material. Alternatively, the PVC resin may be knife coated to both sides of a knitted scrim devoid of openings, or to a non-woven fabric of autogenously bonded polyester fibers, producing a solid continuous layer of supported foam. The PVC compound also includes a plasticizer that imparts a removable nonslip mechanical bond between the shelf liner and an applied surface. Such coverings provide a degree of protective cushioning and are often laminated or fused with a top decorative layer of plastic film. The basic deficiency of foamed non-adhesive liners is that they do not incorporate any provision for the consumer to conveniently alter the product to match the interior dimensions of cabinets or drawers. Moreover, the overall thickness of the shelf liner, along with the variable density of the knitted scrim and thermally cured foam, makes it difficult to maintain the uniform alignment of cuts along the length and width of the material.

Further, prior art methods—which are used to configure cross-tearable features within self-adhesive shelf liners—cannot be successfully applied to form lines of weakness in removable, nonslip, non-adhesive versions that are supported with a knitted scrim or non-woven fabric. The embossment of an intersecting grid of tear lines will not adequately diminish the tensile strength property of the woven yarns or bonded polyester fibers, where the perforation of a linear series of discontinuous holes will not effectively weaken adjacent segments of imperforated substrate. The adaptation of these coverings for hand tearing becomes even less viable with the added combination of a laminated or fused layer of decorative plastic film.

U.S. Pat. No. 5,707,903, issued on Jan. 13, 1998 to H. Schottenfeld, discloses a nonslip laminated liner comprising a foamed PVC coated scrim with a vinyl sheet covering. The scrim increases the tensile strength properties of the foamed nonslip pad, which includes a plurality of open cells extending through the thickness of the cured PVC material. Additionally, the vinyl sheet covering is permanently bonded to the top plane of the nonslip pad.

U.S. Pat. No. 5,854,144, issued on Dec. 29, 1998 to J. Hawley, describes a nonslip multilayer sheet material for covering household surfaces. The cushioned shelf liner is made by laminating a layer of thin plastic film to the top surface of a spunbonded non-woven polyester fabric. The bottom surface of the non-woven fabric is coated with a continuous layer of polyurethane foam.

U.S. Pat. Nos. 5,863,845 and 5,874,371, which respectively issued on Jan. 26, 1999 and Feb. 23, 1999 to T. Owen, similarly disclose a removable non-skid, non-adhesive surface covering comprising a woven substrate having a plurality of apertures, wherein at least a portion of the bottom surface of the substrate is coated with a PVC resin. Alternatively, a non-woven substrate may also be used. The application of the polymeric compound prevents the covering from skidding tangentially or laterally in a plane parallel to an applied surface. A decorative sheet is adhered to the top surface of the non-skid covering.

U.S. Pat. No. 6,022,617, issued on Feb. 8, 2000 to M. Calkins, discloses a laminated nonslip liner or mat having an intermediate layer of non-woven material printed on one side with a pattern of relatively high friction material. The imprinted pattern consists of a high density matrix of latex or PVC projections. A decorative vinyl sheet is laminated to the obverse side of the non-woven material. Similarly, U.S. Pat. No. 6,159,583, issued on Dec. 12, 2000 to the same inventor, discloses a laminated nonslip liner or mat comprising an interposing layer of non-woven material printed with a high density matrix of polyethylene projections. The imprinted thermoplastic resin provides non-adhering, non-marring contact with an underlying surface.

U.S. Pat. No. 6,221,796, issued on Apr. 24, 2001 to J. Hawley et al., describes a laminated shelf lining material having nonslip characteristics. The covering is produced by bonding a smooth continuous layer of vinyl film to a layer of scrim comprising woven threads surrounded by a foamed PVC plastic. Comparatively, U.S. Pat. No. 6,130,174, issued on Oct. 10, 2000 to the same inventor, discloses a smooth surfaced foam laminate and a method for making the material similar to the Hawley '796 patent.

U.S. Pat. No. 7,253,126, issued on Aug. 7, 2007 to W. Browne, discloses a decorative nonslip shelf liner that comprises a multi-layered thermoplastic composite sheet. A decorative top layer of a thin polyvinyl chloride film is laminated or fused to a non-slip bottom layer via a disposed interlayer of polyvinyl chloride plastisol. The non-slip bottom layer consists of a supporting non-woven fabric coated on both sides with a foamed plasticized polyvinyl chloride resin.

U.S. Patent Application Publication US 2003/0036323 A1 by R. Aliabadi, published on Feb. 20, 2003, discloses a multilayered nonslip plastic shelf liner comprising an intermediate layer of fibrous polyester fabric enveloped by two thermally bonded layers of polyvinyl chloride. A thin coating of polyurethane is applied to the obverse side of the covering to provide a smooth frictionless surface, where the reverse side remains uncoated to impart nonslip properties to the laminated material.

None of the above inventions and patents, taken either individually or in combination, is seen to have solved the aforementioned problems associated with resizing removable, nonslip, non-adhesive surface coverings.

Accordingly, it is an object of the present invention to provide a removable, nonslip, non-adhesive covering sheet with an improved composite material having a grid of perforations to facilitate the convenient hand tearing of shelf, drawer or storage liners to size.

It is a further object of the invention to provide a removable, nonslip, non-adhesive covering sheet with a multilayered composite material having a top layer of polymeric film combined to a continuous bottom layer of unsupported calendered foam.

It is yet another object of the invention to provide a removable, nonslip, non-adhesive covering sheet having a top layer of polymeric film that reinforces the dimensional stability of the underling layer of unsupported calendered foam.

Finally, an object of the invention is to provide a removable, nonslip, non-adhesive covering sheet having an underling layer of unsupported calendered foam configured with a fine pattern of micro-embossed indentations to assist in the hand tearing of the material.

These and other objects of the invention will be apparent to those skilled in the art from the following detailed description of the preferred embodiments of the instant invention.

SUMMARY OF THE INVENTION

The disadvantages and limitations of the background art discussed above are overcome by the present invention. With this invention, a removable, nonslip, non-adhesive covering is provided, wherein an improved multilayered composite material having a top decorative layer of polymeric film is combined to a continuous bottom layer of unsupported foam. The structure of the multilayered composite material facilitates the convenient hand tearing of the shelf, drawer or storage liner to size through a grid of perforations oriented along the vertical and horizontal axes of the covering.

In accordance with the present invention, the composite material includes a top layer of polymeric film that reinforces the dimensional stability of the underling layer of unsupported foam. The polymeric film may be combined to the unsupported foam by means of thermal fusion or, alternatively, through the application of an intermediate layer of adhesive. In a specific embodiment, the facing layer may be a polyvinyl chloride sheet, although other synthetic films may be used. The polymeric sheet has sufficient tensile and tear strength properties along the machine and transverse directions of the film to inhibit failure of the multilayered composite material during perforation. The top facing surface of the polyvinyl chloride sheet may be smooth or, more preferably, thermally embossed with a decorative pattern during fusion of the polymeric film to the layer of unsupported foam. By this means, the thermal embossment of the composite material obscures the grid of perforations that penetrate the obverse layer of the shelf, drawer or storage liner.

The underlying layer of unsupported foam consists of a polymeric compound having a diffusion of minuscule gas bubbles. In a preferred embodiment, the polymeric admixture is a polyvinyl chloride resin that includes a chemical foaming agent. The chemical foaming agent is selected from the group of hydrazine derivatives, and is more particularly an Azodicarbonamide powder that is suspended in the resin formulation. Under thermal decomposition, Azodicarbonamide releases nitrogen when exposed to temperatures in the range of 200° to 215° C., thereby causing the expansion of the polymeric composition. The polyvinyl chloride compound is cured by means of a thermal calendering process, wherein the polymeric admixture is uniformly coated on a releasable belt or casting paper which is compressed against a heated roller. In the absence of a knitted scrim or non-woven fabric substrate, the releasable belt or casting paper provides support and dimensional stability to the unsupported polymeric compound while maintaining the uniform thickness of the nonslip material during solidification. The heated roller, releasable belt or casting paper may be configured to impart a fine pattern of micro-embossed indentations on the bottom surface of the unsupported calendered foam. The micro-embossed indentations essentially weaken the tear strength properties of the nonslip layer and enhance the hand alteration of the perforated covering.

The present invention advantageously includes a grid of perforations that are oriented along the vertical and horizontal axes of the multilayered covering. The perforations extend through the profile of the composite material, and are produced with a rotary or flat bed die assembly having a series of perforating rules. The perforating rules consist of a sequence of projecting teeth which are separated at regular intervals by an arrangement of indented gaps. The sequence of projecting teeth incise a linear succession of perforations into the composite material, where the indented gaps form an alternating pattern of uncut tie portions which run adjacent to the incised perforations. The length of the projecting teeth or indented gaps may be of equivalent dimension along the vertical or horizontal axes of the surface covering or, alternatively, may be adapted to compensate for perpendicular variations in the tensile and tear strength properties inherent within the machine and transverse directions of the composite material.

Further objects and advantages of the present invention will be apparent from the following description of the preferred embodiments when considered in conjunction with the accompanying drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
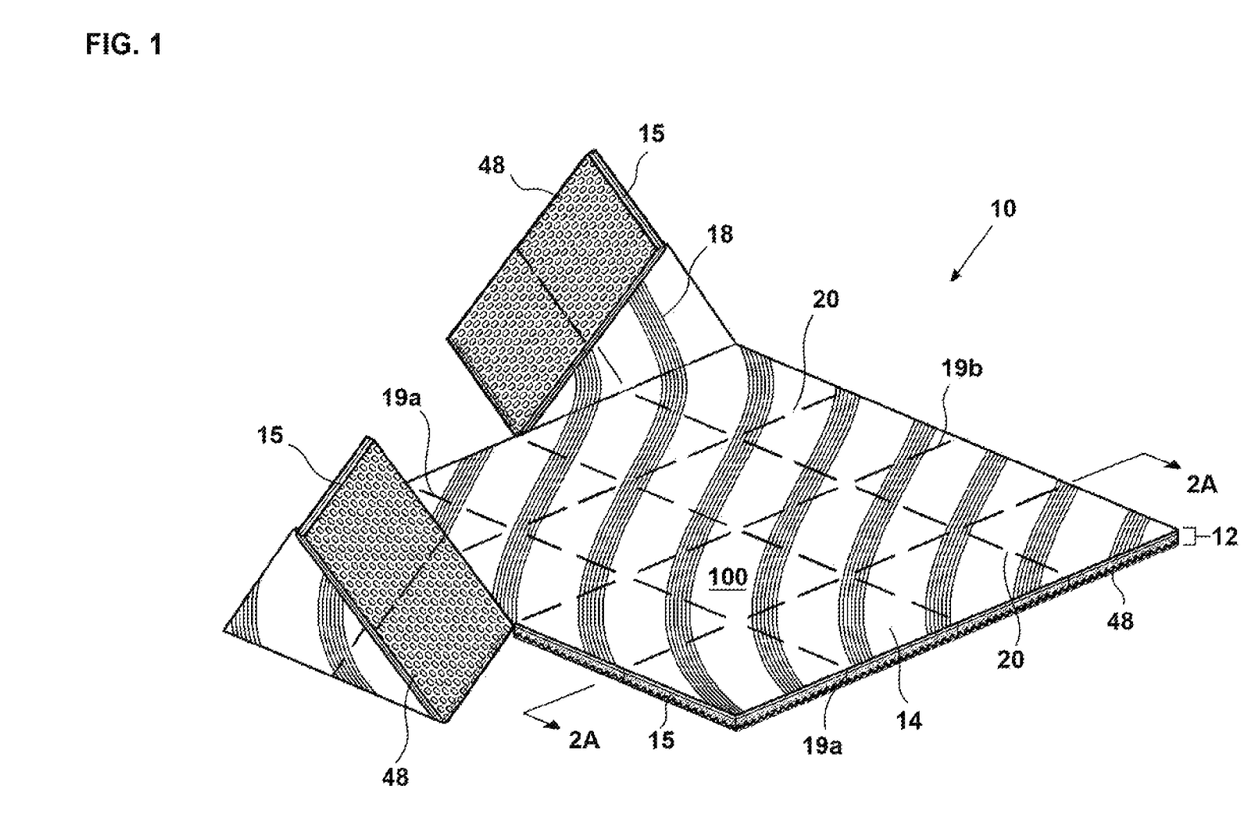
FIG. 1 is an enlarged perspective view of a removable, nonslip, non-adhesive covering according to the present invention, showing a perforated multilayered composite material with torn edge portions.

The present invention is a removable, nonslip, non-adhesive surface covering suitable for use as a shelf, drawer or storage liner, and designated generally as 10 in the drawings. With reference to FIG. 1, the surface covering 10 is a multi-layered composite material 12 having a top facing layer of polymeric film 14 combined to a continuous bottom layer of unsupported foam 15. The structure of the multilayered composite material 12 facilitates the convenient hand tearing of the shelf, drawer or storage liner through a grid of perforations 19a and 19b, which are respectively located along the vertical and horizontal axes of the surface covering 10.

The top facing layer of polymeric film 14 reinforces the dimensional stability of the underling layer of unsupported foam 15. The facing layer 14 may consist of single or multiple layers of thermoplastic film which may be extruded, calendered or cast from the group of polymers that include Polyvinyl Chloride (PVC); Polypropylene (PP); Polyethylene (PE); Polyester (PET); Ethylene Vinyl Acetate (EVA); or other appropriate polymeric formulations. Alternatively, the facing layer 14 may consist of a paper stock having a water resistant coating.

Figure 2A:
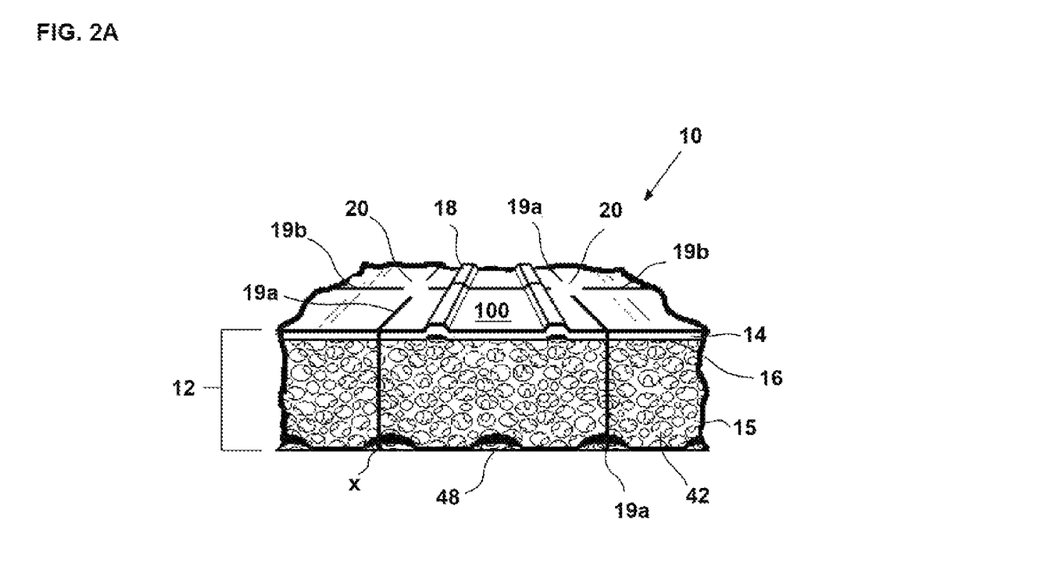
FIG. 2A is a cross-sectional view drawn from lines 2A-2A of FIG. 1, showing the layered construction of a removable, nonslip, non-adhesive covering according to the present invention.
Figure 2B:
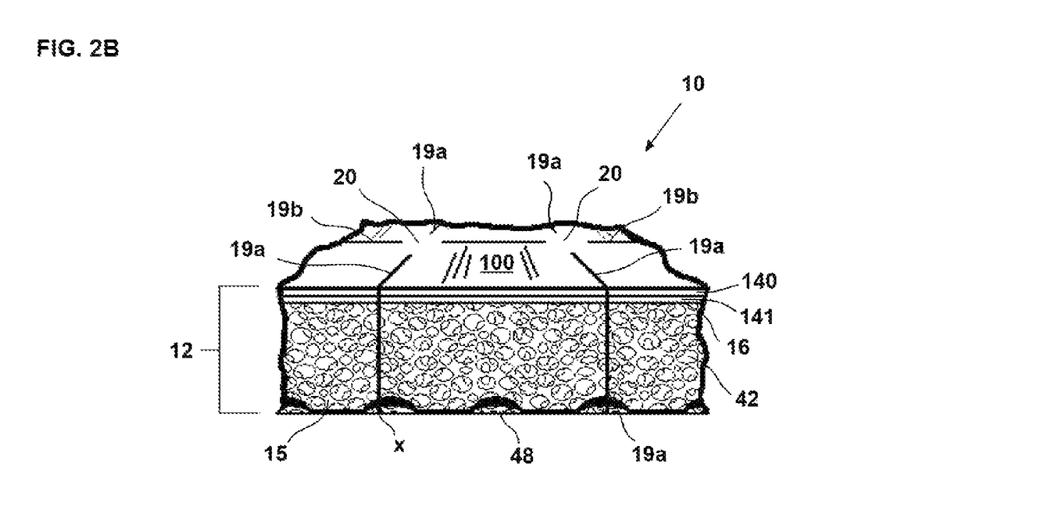
FIG. 2B is a cross-sectional view similar to FIG. 2A showing the layered construction of a first alternate embodiment of a removable, nonslip, non-adhesive covering according to the present invention.
Figure 2C:
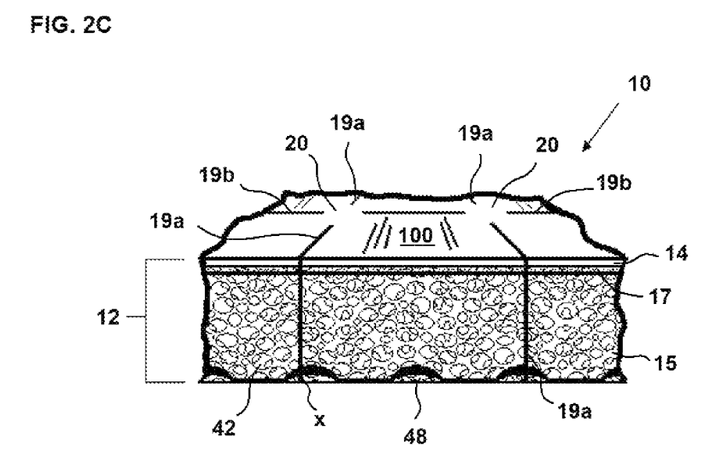
FIG. 2C is a cross-sectional view similar to FIG. 2A showing the layered construction of a second alternate embodiment of a removable, nonslip, non-adhesive covering according to the present invention.

In a preferred embodiment, and as shown in FIG. 2A, the facing layer 14 is composed of a single layer of polyvinyl chloride film that is in the range of 0.075 mm to 0.1775 mm in thickness. The polyvinyl chloride sheet 14 has sufficient tensile and tear strength properties along the machine and transverse directions of the film to inhibit failure of the multilayered composite material 12 during perforation. The preferred tensile strength of the polyvinyl chloride layer 14, when measured according to the standard testing method for tensile properties of thin plastic sheeting under ASTM D-822, is in the range of 175-290 $kg/cm^2$ in the machine direction and 140-270 $kg/cm^2$ in the transverse direction of the polymeric film. Additionally, the tensile modulus of the plastic layer 14, when measured under the same ASTM protocol, is in the preferred range of 130-225 $kg/cm^2$ in the machine direction and 115-200 $kg/cm^2$ in the transverse direction of the film. The preferred tear resistance of the polyvinyl chloride layer 14, when measured according to the standard testing method for tear resistance (Graves Tear) of plastic film and sheeting under ASTM D-1004, is in the range of 50-90 kg/cm for both the machine and transverse directions of the polymeric sheet. The tensile and tear strength properties of the top facing layer 14 may be enhanced by increasing the thickness of the material or, alternatively, by using thermoplastic sheets that are composed of multiple layers of polymeric film 140 and 141, as illustrated in FIG. 2B.

As further shown in FIGS. 2A-2D, the facing layer of polymeric film 14 may be combined to the unsupported foam 15 by means of thermal fusion or, alternatively, through the application of an intermediate layer of adhesive 17. In a preferred embodiment, the facing layer 14 is a single layer of polyvinyl chloride film that is thermally fused to the layer of unsupported foam 15. The thermal fusion of the polyvinyl chloride film 14 and the unsupported foam 15 creates a cohesive bond 16 between the layers of polymeric material, rather than through the lamination of such materials through the application of an intermediate layer of adhesive. In an alternate embodiment, and as disclosed in FIG. 2C, the facing layer 14 and unsupported foam 15 may be laminated through the application of an intermediate layer of adhesive 17. The bonding agent 17 may be selected from the group of synthetic resins that includes Acrylic Polymers, Polyamides, Polyolefins, Polyurethanes, or other suitable adhesive systems. The layer of adhesive 17 may be solidified through the application of heat, ultraviolet light or electron beam curing methods. As an alternative, the adhesive layer 17 may be compounded to be a moisture curable formulation that may reactivate with the application of heat and pressure. Although the facing layer of polymeric film 14 may be a smooth continuous sheet, in a specific embodiment, the top layer is preferably a polyvinyl chloride film that is embossed with a decorative pattern 18. The embossed decorative pattern 18 may be formed under heat and pressure with engraved cylinders or casting papers during the thermal fusion of the top facing layer 14 to the underling layer of unsupported foam 15. The embossed pattern 18 may also be simulated through the application of a rotary screen printed thixotropic resin formulation to the surface of the polymeric film 14. The thixotropic resin may be hardened with ultraviolet light or electron beam curing. The embossment of the composite material 12 obscures the grid of perforations 19a and 19b that penetrate the obverse layer 14 of the shelf, drawer or storage liner 10.

As detailed in FIGS. 2A-2D, and FIG. 3, the underlying layer of unsupported foam 15 consists of a polymeric compound having a diffusion of miniscule gas bubbles 42. The underlying layer of unsupported foam 15 may consist of natural or synthetic resins that include Latex; Polyvinyl Chloride (PVC); Polyurethane (PUR); Ethylene Vinyl Acetate (EVA); or other appropriate compounds. It can be appreciated that the polymeric compound may also contain additives that are standard in the art, including fillers, pigments, matting agents, UV inhibitors, flame-retardants, biocides, fungicides, and other ingredients. In a preferred embodiment, the polymeric compound is a polyvinyl chloride resin that includes a chemical foaming agent. The chemical foaming agent is selected from the group of hydrazine derivatives, and is more particularly an Azodicarbonamide powder that is suspended in the resin formulation. Under thermal decomposition, Azodicarbonamide releases nitrogen when exposed to temperatures in the range of 200° to 215° C., thereby causing the expansion of the polymeric composition.

Figure 4:
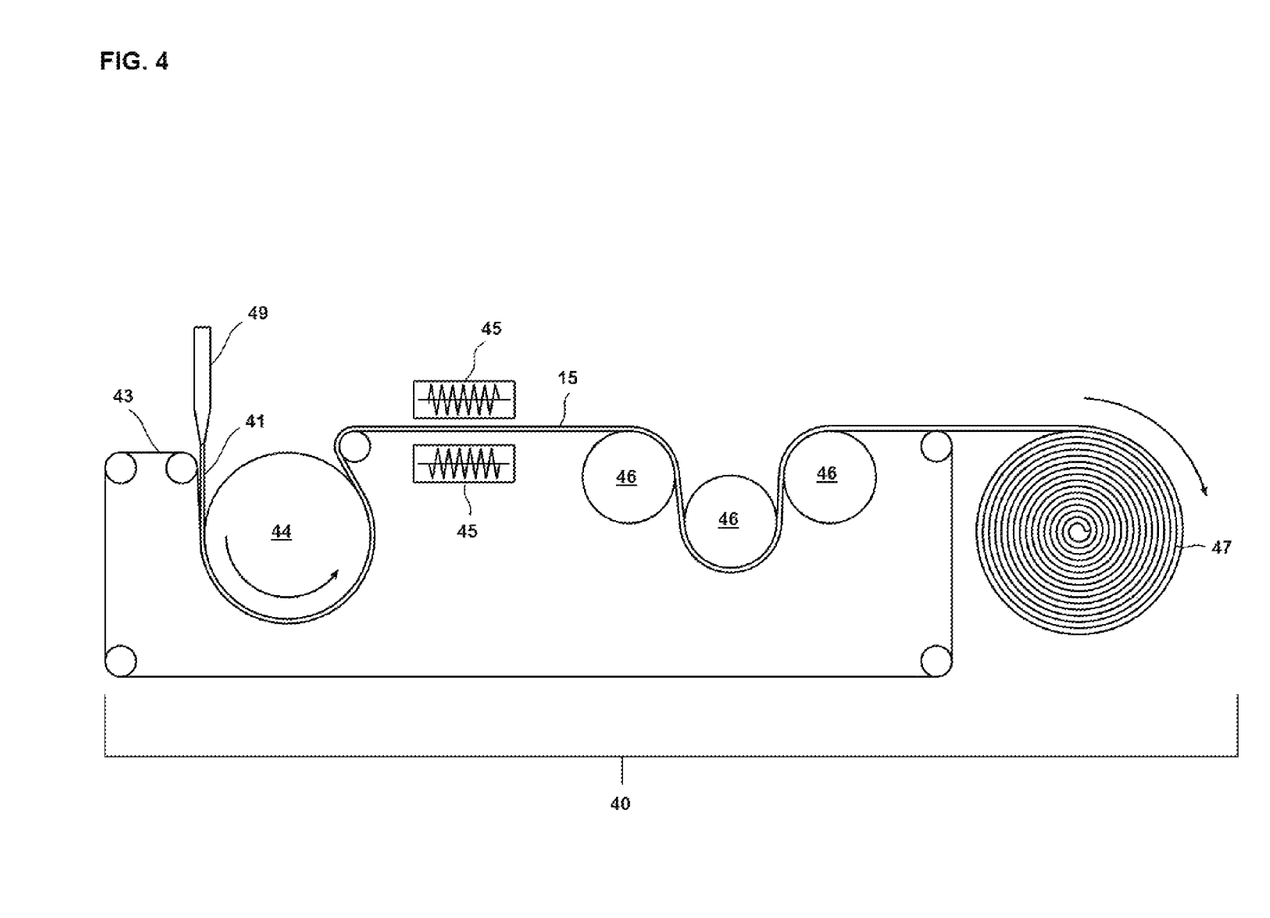
FIG. 4 is a schematic diagram of an apparatus for making a calendered unsupported foamed layer of a removable, non-slip, non-adhesive covering according to the present invention.

The underlying layer of unsupported foam 15 can be made according to the process that is schematically depicted in FIG. 4. The polyvinyl chloride compound 41 is cured by means of a thermal calendering process 40, wherein the polymeric admixture is supplied by metering vat 49 and uniformly coated on a releasable belt 43. The polyvinyl chloride compound 41 and releasable belt 43 are then compressed under tension against a heated roller 44. As an alternative, a releasable casting paper (not shown) may also be used. In the absence of a knitted scrim or non-woven fabric, the releasable belt 43 or casting paper functions as a carrier for the uncured polymeric compound 41. The carrier maintains the uniform thickness of the foam material 15 during thermal solidification. In a preferred embodiment, the layer of unsupported polyvinyl chloride foam 15 is in the range of 1.275 mm to 1.675 mm in thickness. The layer of the polyvinyl chloride foam 15 may be partially solidified as the material exits the heated roller 44, and may be further cured through the use of heated ovens 45. The solidified layer of polyvinyl chloride foam 15 is then cooled through contact with cooling rollers 46, and collected on a take-up roll 47. The uniform layer of cured polyvinyl chloride foam may be smooth on both sides. In a preferred embodiment, the heated roller 44, releasable belt 43 or casting paper is configured to impart a fine pattern of micro-embossed indentations 48. The pattern of micro-embossed indentations 48 are alternately spaced at 0.889 mm intervals, although other micro-embossed configurations may also be used. The micro-embossed indentations 48 essentially weaken the tear strength properties of the unsupported foam 15 and enhance the hand alteration of the perforated surface covering 10.

Figure 2D:
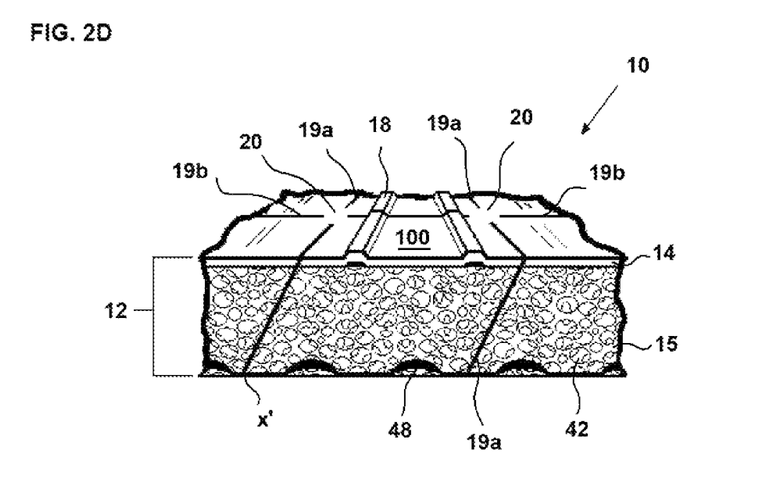
FIG. 2D is a cross-sectional view similar to FIG. 2A showing a perforated bevel configuration of a third alternate embodiment of a removable, nonslip, non-adhesive covering according to the present invention.
Figure 3:
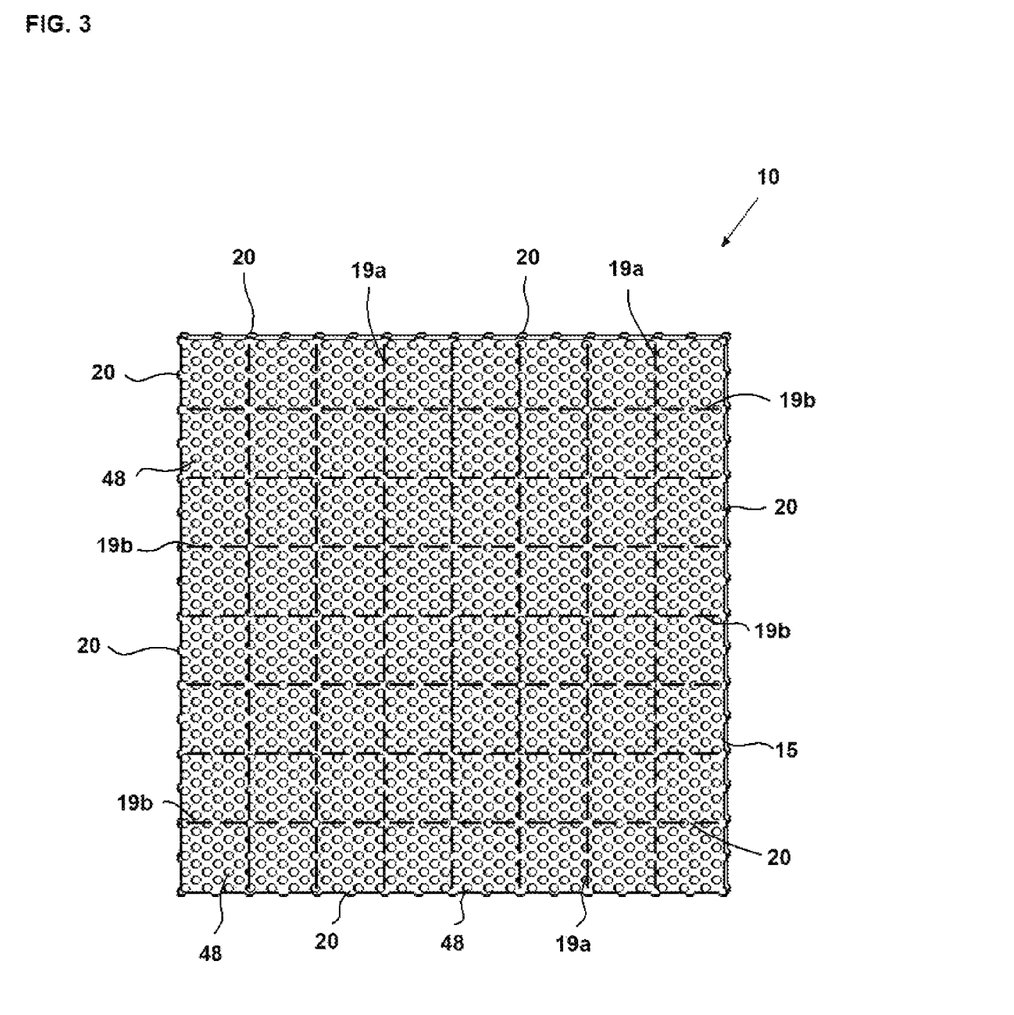
FIG. 3 is a plan view showing micro-embossed indentations formed into the bottom unsupported foamed layer of a removable, nonslip, non-adhesive covering according to the present invention.

With further reference to FIGS. 1, 2A-2D, and FIG. 3, the present invention includes a grid of perforations 19a and 19b that are oriented at right angles along the vertical and horizontal axes of the surface covering 10. The perforations 19a and 19b extend through the profile of the composite material 12, and penetrate the obverse layer 14 of the shelf, drawer or storage liner 10. The perforations 19a or 19b may extend at perpendicular angles x through the profile of the composite material 12 or, as illustrated in FIG. 2D, the perforations 19a or 19b may extend through the composite material at beveled angles x'. In a preferred embodiment, to reduce the visible appearance of perforations scored into the surface of the shelf, drawer or storage liner 10, the perforations 19a and 19b are incised from the bottom of the unsupported foam layer 15 through the obverse layer 14 of the composite material 12. Alternatively, the perforations 19a and 19b may be incised from the obverse layer 14 through the unsupported foam layer 15. In a specific embodiment, the perforations 19a run linearly along the machine direction of the surface covering 10, and are spaced in parallel along the transverse direction of the material in 6.35 mm increments. Conversely, the perforations 19b run linearly along the transverse direction of the surface covering 10, and are spaced in parallel along the machine direction of the material in 6.35 mm increments. Accordingly, the corresponding series of perforations 19a and 19b produce a pattern of interconnecting square portions 100 having all four sides that are approximately 6.35 mm in length. In an alternate embodiment, the parallel arrangement of linear perforations 19a or 19b may not be equidistantly spaced along the machine or transverse directions of the surface covering 10. Moreover, the horizontal or perpendicular arrangement of linear perforations, 19a or 19b, may not be necessarily arranged at corresponding parallel intervals to form a uniform grid along the machine or transverse directions of the shelf, drawer or storage liner 10.

The perforations 19a and 19b are produced with a rotary or flat bed die assembly having a series of perforating rules that are oriented at right angles. As disclosed in FIG. 5, the perforating rules 190 consist of a sequence of projecting teeth 51, which are separated at regular intervals by an arrangement of indented gaps 52. The sequence of projecting teeth 51 incise a linear succession of perforations 19a and 19b into the composite material 12, where the indented gaps 52 form an alternating pattern of uncut tie portions 20 which run adjacent to the incised perforations. In a preferred embodiment, the projecting teeth 51 are each 2.38 mm in length, where the indented gaps 52 span a distance of 0.8128 mm each. In an alternate embodiment, the length of projecting teeth 51, or indented gaps 52, which are machined into the series of perforating rules 190, may be adapted to compensate for perpendicular variations in the tensile and tear strength properties inherent within the machine and transverse directions of the composite material 12. For example, if the tensile and tear strength properties of the composite material 12 are greater in the machine direction, than the tensile and tear strength properties oriented along the transverse direction, the perforating rules 190—which in this instance form the series of linear perforations 19a—would be altered to lengthen the dimension of each projecting tooth 51, while the span of each indented gap 52 would be similarly decreased. Accordingly, modification in the dimensioning of the projecting teeth or indented gaps equalizes the tear resistance of the perforated grid along the vertical and horizontal axes of the surface covering 10.

Figures 5, 6:
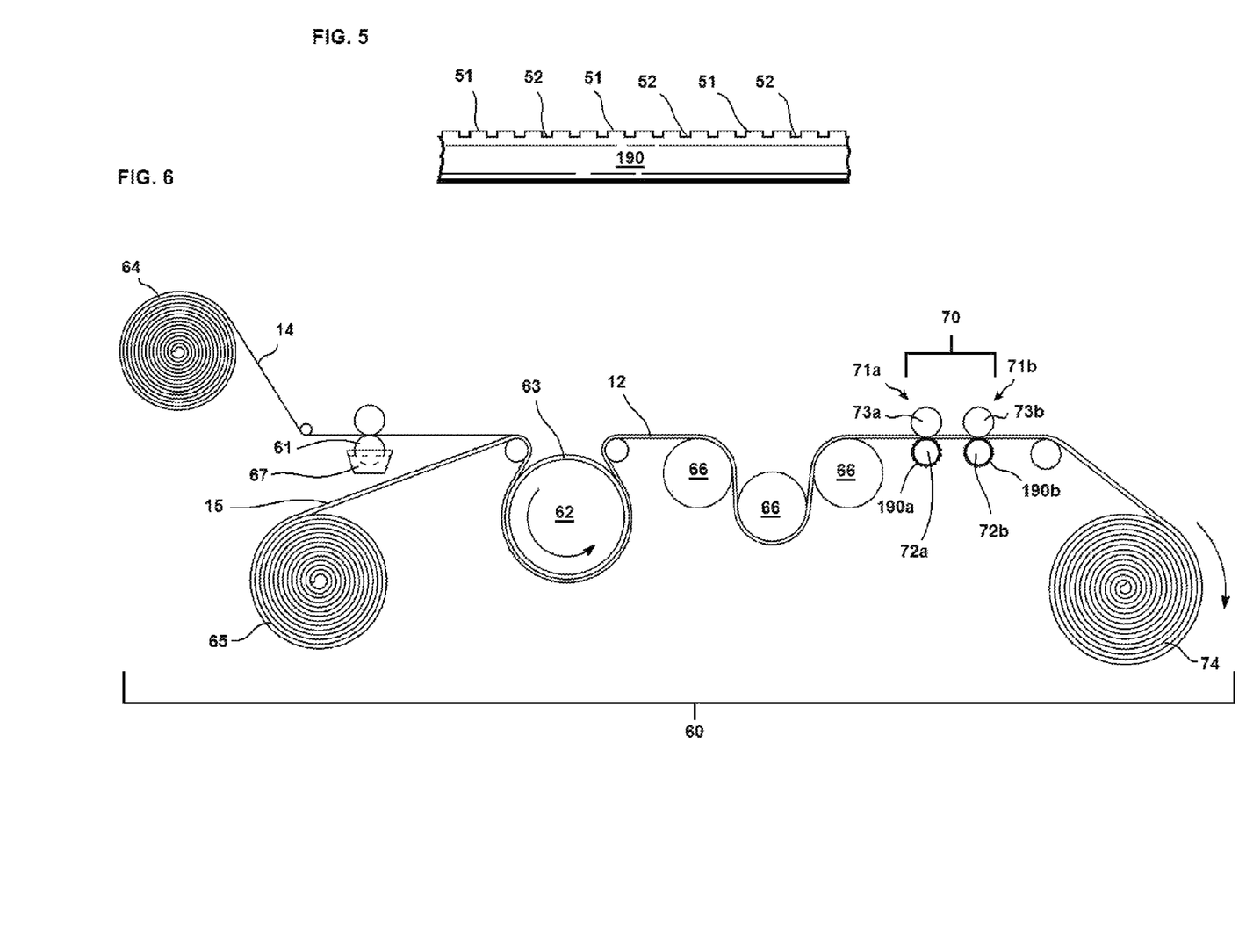
FIG. 5 is a plan view of a perforating rule segment showing a sequence of projecting teeth and indented gaps for perforating a removable, nonslip, non-adhesive covering according to the present invention.
FIG. 6 is a schematic diagram of an apparatus for making a removable, nonslip, non-adhesive covering according to the present invention.

A method for manufacturing the surface covering 10 is schematically illustrated in FIG. 6. The top sheet of polymeric film 14 and bottom layer of unsupported polymeric foam 15 are respectively supplied in roll form 64 and 65. The top sheet of polymeric film and bottom layer of polymeric foam are simultaneously transported under controlled tension to a laminating unit 60 where they are thermally combined. An optional intermediary coating of adhesive 17 may be applied to the underside of the polymeric film 14, or the contacting surface of polymeric foam 15, before the two materials are joined. The adhesive may be applied by way of an anilox roller 61 supplied from an adhesive reservoir 67 or, alternatively, may be spray coated. The facing layer of polymeric film 14 and bottom layer of polymeric foam 15 are then brought together and mutually conveyed under tension around a large heated cylinder 62. The heating process causes the polymeric film 14 and unsupported polymeric foam 15 to become fused together forming a cohesive bond 16. Since the layers are not nipped together during the fusion process, the expanded cellular structure of the polymeric foam 15 does not become permanently compressed, thereby preserving the thickness of the material from thermal deformation.

During the fusion of the composite laminate 12, a decorative pattern 18 may be optionally embossed into the facing layer of the polymeric film 14 by way of an engraved sleeve 63 that is removably secured to the heated cylinder 62. Alternatively, the embossed pattern 18 may be formed into the facing layer of the polymeric film 14 through the use of a casting paper (not shown). The casting paper is supplied in rolled form and wrapped under tension and in direct contact around the heated cylinder 62. Under heat and tension, the composite material 12 assumes the embossed pattern 18 that is engraved into the removable sleeve 63 or contoured into the casting paper. The combined layers of the composite laminate 12 are then passed through a series of cooling rollers 66 to set the cohesive bond 16 and embossed pattern 18.

After fusing, embossment and cooling of the composite material 12, the laminated web is die cut with a grid of perforations 19a and 19b which are oriented at right angles along the vertical and horizontal axes of the surface covering 10. To ensure the perpendicular accuracy of the incised perforations 19a and 19b, the laminated material 12 is preferably passed between a two-stage rotary die assembly 70, which is comprised of two rotary die cutters 71a and 71b. Each rotary die cutter includes a rotatable knife cylinder 72a or 72b having perforating rules 190a or 190b that are fixed on each circumference thereof. The respective die cutters 71a and 71b also include an anvil cylinder 73a or 73b, made rotatable in a face-to-face relation to and in synchronism with the knife cylinders 72a or 72b. The two rotary die cutters 71a and 71b subject the laminated material 12 to a predetermined cutting treatment by feeding the web through the central converging portions of cylinders 72a and 73a, and then again through cylinders 72b and 73b. To inhibit failure of the multilayered composite material 12 during perforation, the linear succession of perforations 19a, which run along the machine direction of the web, are incised first with rotary die cutter 71a. The complementary arrangement of linear perforations 19b, which run along the transverse direction of the web, are then incised with rotary die cutter 71b. The shelf, drawer or storage liner 10 is then collected on take-up roll 74. It can be appreciated by those skilled in the art that the grid of perforations 19a and 19b may be concurrently incised into the composite material 12 with a rotary die cutter having a grid of perforating rules machined on a single rotatable knife cylinder.

Even though numerous characteristics and advantages of the present invention have been set forth in the foregoing description, together with details of the structure and function of the preferred embodiments, the above disclosure is illustrative only. Changes may be made in detail, especially in matters of shape, size and arrangement of parts within the principles of the invention to the full extent indicated by the broad general meaning of the terms in which the appended claims are expressed.

The invention claimed is:

1. A surface covering consisting of:
a multilayered composite material, wherein the multilayered composite material further includes a plurality of vertical perforated lines and a plurality of horizontal perforated lines, the vertical and horizontal perforated lines forming a grid, the structure of said multilayered composite material facilitating the convenient hand tearing of said surface covering through said grid;
and further wherein the multilayer composite material further comprises (1) a top facing layer of polymeric film, wherein the top facing layer comprises single or multiple layers of a thermoplastic film and (2) a non-slip, non-adhesive bottom layer of unsupported polyvinyl chloride foam, wherein said top facing layer reinforces the dimensional stability of the unsupported foam and further still has sufficient tensile and tear strength to inhibit failure of said surface covering during tearing and the unsupported polyvinyl chloride foam is configured to tear, along with the polymeric film, along the vertical and horizontal perforated lines.

2. The surface covering according to claim 1, wherein the top facing layer comprises a single layer of polyvinyl chloride film.

3. The surface covering according to claim 2, wherein the single layer of polyvinyl chloride film has a thickness of about 0.075 mm to 0.1775 mm.

4. The surface covering according to claim 1, further comprising an embossed pattern on the top facing layer of polymeric film.

5. The surface covering according to claim 1, wherein the non-slip, non-adhesive bottom layer of unsupported polyvinyl chloride foam has a thickness of about 1.275 mm to 1.675 mm.

6. The surface cover according to claim 1, wherein the non-slip, non-adhesive bottom layer of unsupported polyvinyl chloride foam is configured with a fine pattern of micro-embossed indentations for weakening a tear strength of the unsupported foam.

7. The surface covering according to claim 1, wherein the non-slip, non-adhesive bottom layer of unsupported polyvinyl chloride foam has a smooth continuous surface.

8. The surface covering according to claim 1, wherein the surface covering is a shelf liner, a drawer liner and/or a storage container liner.

9. The surface covering according to claim 1, wherein the polymeric film has a tensile strength in the range of 175-290 kg/cm$^2$ in the machine direction and 140-270 kg/cm$^2$ in the transverse direction, a tensile modulus in the range of 130-225 kg/cm$^2$ in the machine direction and 115-200 kg/cm2 in the transverse direction, and a tear resistance in the range of 50-90 kg/cm$^2$ in each of the machine and transverse directions.

10. A surface covering comprising:
a multilayered composite material, wherein the multilayered composite material further includes a plurality of vertical perforated lines and a plurality of horizontal perforated lines, the vertical and horizontal perforated lines forming a grid, the structure of said multilayered composite material facilitating the convenient hand tearing of said surface covering through said grid;
and further wherein the multilayer composite material further comprises (1) a top facing layer of paper and (2) a non-slip, non-adhesive bottom layer of unsupported polyvinyl chloride foam, wherein said top facing layer reinforces the dimensional stability of the unsupported foam and further still has sufficient tensile and tear strength to inhibit failure of said surface covering during tearing, wherein at least one the plurality of vertical perforated lines and the plurality of horizontal perforated lines is formed at an angle other than 90 degrees relative to a bottom surface of the bottom layer of unsupported foam.

11. The surface covering according to claim 10 wherein the top facing layer of paper is adhered to the non-slip, non-adhesive bottom layer of unsupported polyvinyl chloride foam with an interposing layer of adhesive.

12. The surface covering according to claim 10, wherein the polymeric film has a tensile strength in the range of 175-290 kg/cm$^2$ in the machine direction and 140-270 kg/cm$^2$ in the transverse direction, a tensile modulus in the range of 130-225 kg/cm$^2$ in the machine direction and 115-200 kg/cm$^2$ in the transverse direction, and a tear resistance in the range of 50-90 kg/cm$^2$ in each of the machine and transverse directions.

13. A surface covering consisting of:
a multilayered composite material, wherein the multilayered composite material further includes a plurality of vertical perforated lines and a plurality of horizontal perforated lines, the vertical and horizontal perforated lines forming a grid, the structure of said multilayered composite material facilitating the convenient hand tearing of said surface covering through said grid;
and further wherein the multilayer composite material further comprises (1) a top facing layer of polymeric film, wherein the top facing layer comprises single or multiple layers of a thermoplastic film and (2) a non-slip, non-adhesive bottom layer of unsupported foam, wherein said top facing layer reinforces the dimensional stability of the unsupported polyvinyl chloride foam and further still has sufficient tensile and tear strength to inhibit failure of said surface covering during tearing and further comprising an adhesive layer in-between the top facing layer of polymeric film and the non-slip, non-adhesive bottom layer of unsupported foam; and
an embossed pattern on the top facing layer of polymeric film, wherein the embossed pattern is formed so as to obscure the grid of the vertical and horizontal perforated lines;
wherein a bottom surface of the bottom layer of unsupported polyvinyl chloride foam is configured with a fine pattern of micro-embossed indentations for weakening a tear strength of the unsupported foam due to the vertical and horizontal perforated lines intersecting the indentations.

14. The surface covering according to claim 13, wherein the polymeric film has a tensile strength in the range of 175-290 kg/cm$^2$ in the machine direction and 140-270 kg/cm$^2$ in the transverse direction, a tensile modulus in the range of 130-225 kg/cm$^2$ in the machine direction and 115-200 kg/cm$^2$ in the transverse direction, and a tear resistance in the range of 50-90 kg/cm$^2$ in each of the machine and transverse directions.

* * * * *